United States Patent [19]

Schneider

[11] Patent Number: 4,867,305

[45] Date of Patent: Sep. 19, 1989

[54] RELEASE OF STERILIZED DENTAL BIT PACKAGING

[76] Inventor: Heidemarie Schneider, 2706 McArthur Way, Lehigh Acres, Fla. 33936

[21] Appl. No.: 142,498

[22] Filed: Jan. 11, 1988

Related U.S. Application Data

[63] Continuation-in-part of Ser. No. 41,421, Apr. 23, 1987, abandoned.

[51] Int. Cl.[4] ............................................. A61B 19/02
[52] U.S. Cl. .................................. 206/63.5; 206/368; 206/230; 206/379
[58] Field of Search ...................... 206/15.2, 230, 363, 206/368, 369, 379, 305, 306, 572, 63.5; 433/3, 77, 79, 165

[56] References Cited

U.S. PATENT DOCUMENTS

| | | | |
|---|---|---|---|
| 2,964,045 | 12/1960 | Otto et al. | 206/15.2 |
| 4,061,220 | 12/1977 | Essen | 206/306 |
| 4,445,611 | 5/1984 | Shofu | 206/379 |
| 4,503,392 | 3/1985 | Nelligan et al. | 206/379 |

FOREIGN PATENT DOCUMENTS 1303573  8/1962  France .................. 206/230
2505299 11/1982  France .................. 206/379

Primary Examiner—David T. Fidei
Attorney, Agent, or Firm—Alfred E. Wilson

[57] ABSTRACT

My copending application Ser. No. 41,421 filed Apr. 23, 1987, now abandoned disclosed a (throw-away) packaging construction for Sterilized Dental Bits. These drill bits are so constructed and arranged that it is unnecessary for the Dentist or his assistant to touch the drill bits prior to the time that the bits are used with respect to each particular patient. The necessity for this construction came about to overcome the fear that many dental patients have of being contaminated by a communicable disease such as "Aids", where the Dentist or his assistant touches the drill bits used to drill out decayed portions of teeth that need "filling", or where a drill bit is used that has been previously used on another patient. My copending application discloses individual drill bits packaged in individual containers and closed by individualized closure members after the drill bits have been sterilized. In the event that difficulties are encountered in removing the drill bit from the chuck or the container, one end of the container package can be provided with a circumferential extension having cross slots into which the shank of the drill bit can be clamped to force the drill bit to be released.

3 Claims, 1 Drawing Sheet

RELEASE OF STERILIZED DENTAL BIT PACKAGING

RELATION TO PENDING APPLICATION

This is a continuation in part of my copending application Ser. No. 41,421 filed Apr. 23, 1987, now abandoned.

SUMMARY OF THE INVENTION

While my copending application provides individualized protection for sterilized drill bits used to drill out decayed portions of teeth that need "filling", difficulties are encountered on occasion in releasing the drill bits from the chuck. To guard against such a contingency I provide a slotted annular ring type extension on the container or closure member. The driving shank of the drill bit can be projected into the spaced slots of the annular ring, and can be firmly gripped by twisting the container or closure member to clamp the drill bit which can then be released.

DESCRIPTION OF THE PREFERRED EMBODIMENT

Figure 1:
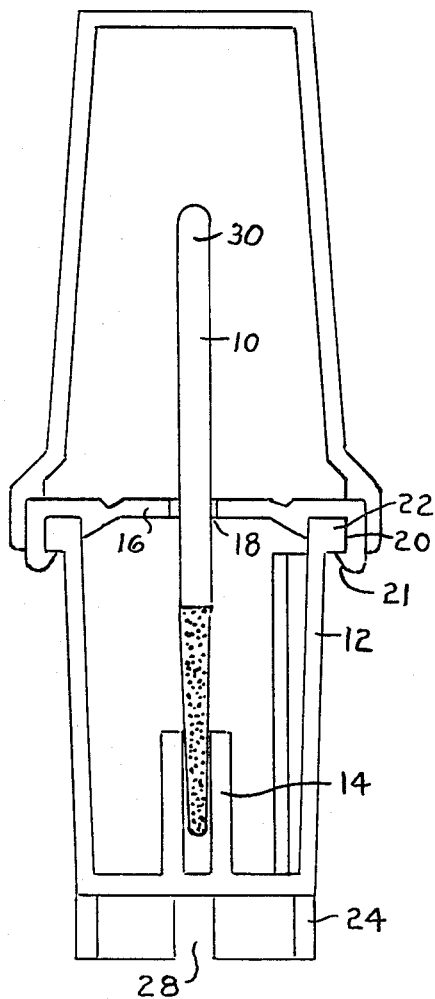
FIG. 1 is a side elevational view of the sterilized dental bit package with the slotted annular ring secured thereto.
Figure 2:
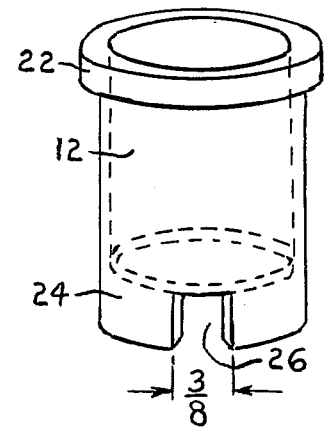
FIG. 2 is a perspective view of the container with the slotted annular ring.
Figure 3:
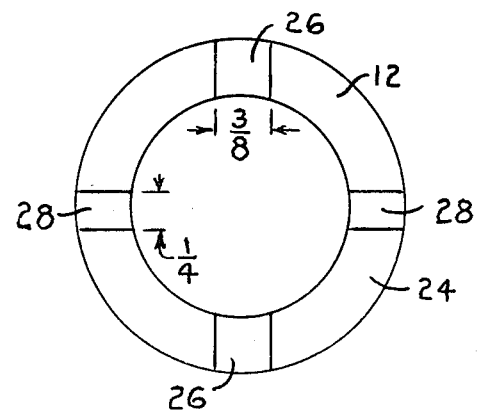
FIG. 3 is an end elevational view of the container illustrating the slotted ring to engage and clamp the drill bit.

Referring now to the drawings a drill bit 10 which may be of a wide variety of drilling materials and drilling contours and degrees of coarseness may be positioned in a container 12 and be suitably supported in a contoured pedestal 14. The drill bit 10 is resiliently held upright in the container 12 by a resilient sealing cap 16 having a central aperture 18 through which the drill bit 10 projects.

The cap 16 has an axially extending outer flange 20 having an inwardly contracted flange 20 to overlie and engage an enlarged rim 22 formed around the top of the container 12 to securely hold the drill bit 10 in the container 12 which is substantially sealed by the sealing cap 16.

The container 12 has an annular ring 24 at the closed end of the container 12. The annular ring 24 has aligned slots 26 and 28 of different widths across the annular ring. The slots 26 and 28 are of a width to receive the shank 30 of the drill bit 10 by which the drill bit is engaged by the chuck of the driving motor by which the drill bit is rotated. The drill bit 10 can then be clamped to hold it without the necessity of the Dentist or his assistant touching the drill bit. The drill bit can thus be released, and can be placed in a sterilized container for reuse with the same patient if the need for a drill of the same character and degree of coarseness occurs while the Dentist or his assistant is working with the same patient. When the dental work with that particular patient is finished the used drill can be discarded as a "throw away" item.

The operation of releasing a drill bit from its driving chuck is achieved by placing the exposed shank of the drill bit 10 in the aligned slots 26 or 28 of the annular ring 24 of the container 12 and twisting the container to exert a clamping force on the drill bit 10. The drill bit can then be rotated slightly whereupon it will be released and can then be removed.

I claim:

1. A holder for a dental drill bit having a driving shank and an abrasive cutting end comprising an open ended container having a support for the drill bit, a resilient releasable apertured cap to engage the open end of the container and having a central aperture to engage the shank of the drill bit and to support it in alignment with the drill bit support, the container having a slotted annular ring at its closed end for the reception of the shank of the drill bit.

2. The invention defined in claim 1 wherein the annular ring of the container has cross slots for the reception of the driving shanks of dental bits.

3. In a dental drill bit holder to dispense drill bits having driving shanks under conditions whereby it is unnecessary for the Dentist to touch the drill bit with his hand prior to using it to drill the patient's teeth, and wherein the drill bit is positioned in an open ended container having a drill bit support, and a closure over the container and a transversely slotted annular ring extending beyond the closed end of the container, and wherein a driving chuck engages the shank of the drill bit, the method of removing the drill bit from the driving chuck which comprises the steps of positioning the shank of the drill bit in the slotted annular ring and exerting pressure between the container and the driving chuck to release the drill bit from the driving chuck.

* * * * *